United States Patent [19]
Felder et al.

[11] Patent Number: 5,882,920
[45] Date of Patent: *Mar. 16, 1999

[54] APPARATUS FOR DETERMINING THE PRESENCE OR ABSENCE OF A PARAFFINOPHILIC MICROORGANISM

[75] Inventors: Mitchell S. Felder, Hermitage; Robert A. Ollar, Milford, both of Pa.

[73] Assignee: Infectech, Inc., Sharon, Pa.

[ * ] Notice: The term of this patent shall not extend beyond the expiration date of Pat. No. 5,654,194.

[21] Appl. No.: 939,793

[22] Filed: Sep. 29, 1997

Related U.S. Application Data

[62] Division of Ser. No. 555,734, Nov. 9, 1995, Pat. No. 5,707,824.

[51] Int. Cl.$^6$ ...................................................... G12M 1/16
[52] U.S. Cl. .................................. 435/287.9; 435/288.1; 435/288.3; 435/810
[58] Field of Search ..................................... 435/3, 30, 34, 435/32, 33, 287.1, 286.1, 286.5, 287.9, 288.1, 288.3, 304.1, 305.1, 307.1, 309.1, 810

[56] References Cited

U.S. PATENT DOCUMENTS

| | | |
|---|---|---|
| 3,826,717 | 7/1974 | Gilbert et al. . |
| 4,683,195 | 7/1987 | Mullis et al. . |
| 4,683,201 | 7/1987 | Hamill et al. . |
| 4,683,202 | 7/1987 | Mullis . |
| 5,153,119 | 10/1992 | Ollar . |
| 5,316,918 | 5/1994 | Ollar . |
| 5,654,194 | 8/1997 | Felder et al. . |
| 5,668,010 | 9/1997 | Felder et al. . |

OTHER PUBLICATIONS

Fuhs, G.W., "Der Mikrobielle Abbau Von Kohlenwasserstoffen", *Arch. Mikrobiol.*, 39:374–422 (1961).

Mishra, S.K. et al., "Observations On Paraffin Baiting As A Laboratory Diagnostic Procedure In Nocardiosis", *Mycopathologica and Mycologia Applicatia*, vol. 51, 2–3, pp. 147–157 (1973).

Ollar, R.–A., "A Paraffin Baiting Technique That Enables A Direct Microscopic View Of in situ Morphology Of *Nocardia asteroides* With The Acid–Fast Or Fluorescence Staining Process", *Zbl. Bakt. Hyg., I. Abt. Orig. A 234*, pp. 81–90 (1976).

Wolinsky, E., "Nontuberculous Mycobacteria And Associated Diseases", *American Review of Respiratory Disease*, vol. 119: 107–159 (1979).

Horsburgh, C.R., Jr. et al., "Disseminated Infection with *Mycobacterium avium–intracellualare*", *Medicine*, vol. 64, No. 1: 36–48 (1983).

Murphey, S.A. et al., "*Mycobacterium Avium–Intracellulare* In A Hospital Hot Water System: Epidemiologic Investigation", *American Society for Microbiology*, 277 (1983).

(List continued on next page.)

*Primary Examiner*—William H. Beisner
*Attorney, Agent, or Firm*—David V. Radack; Eckert Seamans Cherin & Mellott, LLC

[57] ABSTRACT

A method of determining the presence of a paraffinophilic microorganism in a specimen taken from a patient. The method includes providing a receptacle containing an aqueous solution and adjusting the solution to mimic the in vivo clinical conditions of the patient. The method then further includes inoculating the solution with the specimen and then placing in the receptacle a paraffin coated slide to bait the paraffinophilic microorganism. The slide is then analyzed after exposure to the specimen to determine the presence or absence of the paraffinophilic microorganism. An associated apparatus is also disclosed.

4 Claims, 3 Drawing Sheets

OTHER PUBLICATIONS

Kirihara, J.M. et al., "Improved Detection Times For *Mycobacterium avium* Complex And *Mycobacterium tuberculosis* With The BACTEC Radiometric System", *Journal of Clinical Microbiology*, pp. 841–845 (Nov. 1985).

Reichert, C.M. et al., "Pathologic Features Of Aids", *AIDS: Etiology, Diagnosis, Treatment and Prevention*, pp. 111 and 134, J.B. Lippincott Company (1985).

Hawkins, C.C. et al., "*Mycobacterium avium* Complex Infections In Patients With The Acquired Immunodeficiency Syndrome", *Annals Of Internal Medicine*, 105:184–188 (1986).

Gonzalez, R. et al., "Evaluation Of Gen–Probe DNA Hybridization Systems For The Identification Of *Mycobacterium tuberculosis* And *Mycobacterium avium–intracellulare*", *Diagn. Microbiol. Infect. Dis.*, 8:69–77 (1987).

Klatt, E.C. et al., "Pathology Of *Mycobacterium avium–intracellulare* Infection In Acquired Immunodeficiency Syndrome", *Human Pathology*, vol. 18, No. 7: 709–714 (Jul. 1987).

Wallace, J.M. et al., "*Mycobacterium avium* Complex Infection In patients With The Acquired Immunodeficiency Syndrome* A Clinicopatholgic Study", *Chest*, 93 (5), pp. 926–932 (1988).

Heifets, L. et al., "Comparison Of Bactericidal Activities Of Streptomycin, Amkiacin, Kanamycin, And Capreomycin Against *Mycobacterium avium* And *Mycobacterium tuberculosis*", *Antimicrobial Agents and Chemotherapy*, pp. 1298–1301 (Aug. 1989).

Hurley, S.S. et al., "Development Of A Diagnostic Test For Johne's Disease Using A DNA Hybridization Probe", *Journal of Clinical Microbiology*, pp. 1582–1587 (Jul. 1989).

Horsburgh, C.R., Jr. et al., "The Epidemiology Of Disseminated Nontuberculous Mycobacterial Infection In The Acquired Immunodeficiency Syndrome (AIDS)", *American Review of Respiratory Disease*, 139: 4–7 (1989).

Ma, P. et al., "Definitive Diagnostic Methods For Diseases Indicative Of AIDS", *AIDS and Infections of Homosexual Men*, Second Edition, pp. 233–234 Butterworth Publishers (1989).

Hoy, J. et al, "Quadruple–Drug Therapy For *Mycobacterium avium–intracellulare* Bacteremia In AIDS Patients", *The Journal of Infectious Diseases*, 161:801–805 (Apr. 1990).

Inderlied, C.B. et al., "Disseminated *Mycobacterium avium* Complex Infection", *AIDS Clinical Review*, pp. 165–191 (1990).

Kemper, C.A. et al., "Microbiologic And Clinical Response Of Patients With AIDS and MAC Bacteremia To A Four Oral Drug Regimen", *American Society for Microbiology*, (*Abstract*), p. 297 (1990).

Ollar, R.–A. et al., "The Use Of Paraffin Wax Metabolism In The Speciation Of *Mycobacterium avium–intracellulare*", *Tubercle*, 71, pp. 23–28, Longman Group UK, Ltd. (1990).

Bermudez, L.E. et al., "An Animal Of *Mycobacterium avium* Complex Disseminated Infection After Colonization Of The Intestinal Tract", *The Journal of Infectious Diseases*, 165:75–79 (Jan. 1992).

Havlik, J.A., Jr. et al., "Disseminated *Mycobacterium avium* Complex Infection: Clinical Identification And Epidemiologic Trends", *The Journal of Infectious Diseases*, 165: 577–580 (Mar. 1992).

Kemper, C.A. et al., "Treatment Of *Mycobacterium avium* Complex Bacteremia In AIDS With A Four–Drug Oral Regimen", *Annals of Internal Medicine*, 116, No. 6: 466–472 (Mar. 1992).

APPARATUS FOR DETERMINING THE PRESENCE OR ABSENCE OF A PARAFFINOPHILIC MICROORGANISM

This is a division of application Ser. No. 08/555,734, filed Nov. 9, 1995, now U.S. Pat. No. 5,707,824.

BACKGROUND OF THE INVENTION

This invention relates to a method of identifying a paraffinophilic microorganism using various milieus and an associated apparatus and, more particularly, to a receptacle containing an aqueous solution that mimics the in vivo conditions of a patient. A paraffin coated slide is used to bait a paraffinophilic organism that can grow on the slide. The organism then can be identified by a number of different methods.

U.S. Pat. Nos. 5,153,119 and 5,316,918, the disclosures of which are incorporated by reference herein, disclose methods and apparatus for identifying and testing the antibiotic sensitivity of *Mycobacterium avium*-intracellulare ("MAI"). One of the co-inventors herein, Robert-A. Ollar, was the named inventor on these patents. The method of identifying MAI includes placing a paraffin coated slide in a receptacle containing a sterile aqueous solution inoculated with a specimen from a patient and analyzing the slide after exposure to the specimen to determine the presence or absence of MAI. The analysis step involves performing a number of speciation assays, such as a tellurite reduction test. The method for testing the sensitivity of MAI to different antimicrobial agents and dosages thereof includes providing a plurality of test tubes adapted to contain an amount of an antimicrobial agent to be tested and MAI to be assayed and a separate paraffin coated slide adapted for placement in each of the test tubes. Observing the growth of MAI on the slide can be used to determine the concentration of the antimicrobial agent necessary to resist MAI growth on the slide.

The inventions provide effective, efficient and economical methods for identifying MAI and testing MAI for antimicrobial agent sensitivity. These methods avoid the use of expensive, complicated equipment, and thus can be used in places such as field hospitals and third world locations where the more expensive and hard to use equipment is not available.

Despite the effectiveness of the methods and apparatus disclosed in the above-mentioned patents, it would be desired to refine the process of identifying MAI, as well as other paraffinophilic microorganisms.

SUMMARY OF THE INVENTION

The invention has met or surpassed the above-mentioned need as well as others. The method of determining the presence of a paraffinophilic microorganism in a specimen taken from a patient includes providing a receptacle containing an aqueous solution and adjusting the solution to mimic the in vivo clinical conditions of the patient. The method further includes inoculating the solution with the specimen and then placing in the receptacle a paraffin coated slide. The slide is then analyzed after exposure to the specimen to determine the presence or absence of the microorganism.

An apparatus to facilitate determination of the presence or a paraffinophilic microorganism in a specimen taken from a patient is also provided. The apparatus comprises a receptacle for holding an aqueous solution and a paraffin coated slide adapted to be placed in the receptacle. The apparatus further comprises means for adjusting the aqueous solution to mimic the in vivo clinical conditions of the patient.

BRIEF DESCRIPTION OF THE DRAWINGS

A full understanding of the invention can be gained from the following detailed description of the invention when read in conjunction with the following drawings.

DETAILED DESCRIPTION

As used herein, the term "patient" refers to a member of the animal kingdom, including human beings whose body specimen is being processed by the method and apparatus of the invention.

As used herein, the term "paraffinophilic" means an organism that can employ paraffin as a source of carbon in a basal salt media, devoid of other forms of carbon, the organism can be bacterial or fungal in nature.

Figure 1:
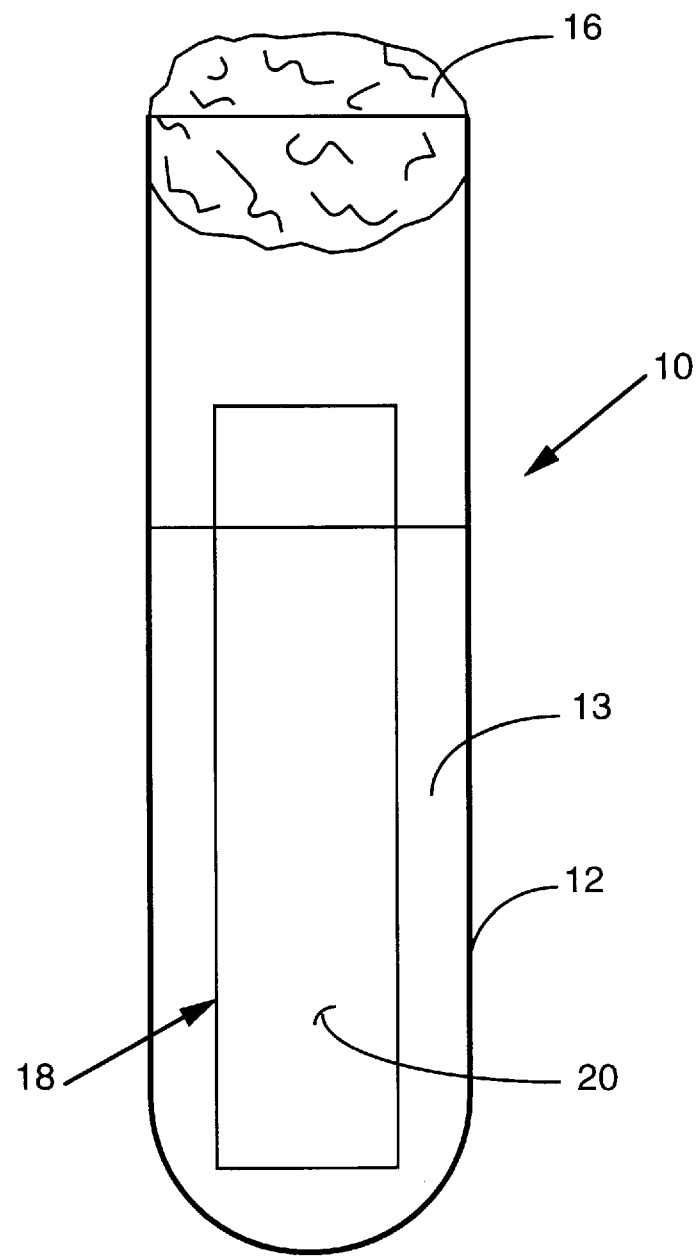
FIG. 1 is a front elevational view of a test tube holding a paraffin coated slide in an aqueous solution inoculated with a specimen.

The method and apparatus of the invention provide an efficient, effective and economical way of identifying a paraffinophilic microorganism. Referring to FIG. 1, one embodiment of a paraffinophilic microorganism identification apparatus 10 is shown. The apparatus 10 includes a standard test tube 12 which contains an aqueous solution 13 (such as distilled water) and a cotton plug 16 to seal the test tube 12. A specimen to be tested for the presence or absence of a paraffinophilic microorganism is inoculated into the aqueous solution 13. A slide 18, having a coating of paraffin 20 is then placed into the test tube 12. It will be appreciated that the aqueous solution 13 should not. contain any carbon source, as it is desired to provide a sole carbon source on the slide in order to effectively grow the microorganism to be identified on the slide 18 and not in the aqueous solution 13. Growth on the paraffin coated slide 18 can be analyzed to determine the presence or absence of a paraffinophilic microorganism. Such tests to analyze the growth can include tests such as DNA hybridization or can be tests for specific paraffinophilic microorganisms, such as MAI, as is disclosed in U.S. Pat. Nos. 5,153,119 and 5,316,918, the disclosures of which are specifically incorporated by reference herein.

The specimen to be inoculated into the test tube 12 can be a blood sample; any biopsy or tissue specimen; stomach fluid; urine; cerebral spinal fluid; nasopharyngeal mucosa or saliva. These specimens can be obtained from the patient in the doctor's office or in the emergency room of a hospital, for example, by known techniques in known standard ways.

The paraffin 20 included on the slide is used to bait the paraffinophilic microorganism. For example, the paraffin can be used to bait MAI. It will be appreciated that the aqueous solution 13 should not contain any carbon source, as it is desired to provide a sole carbon source on the slide in order to effectively identify the microorganism.

Figure 2:
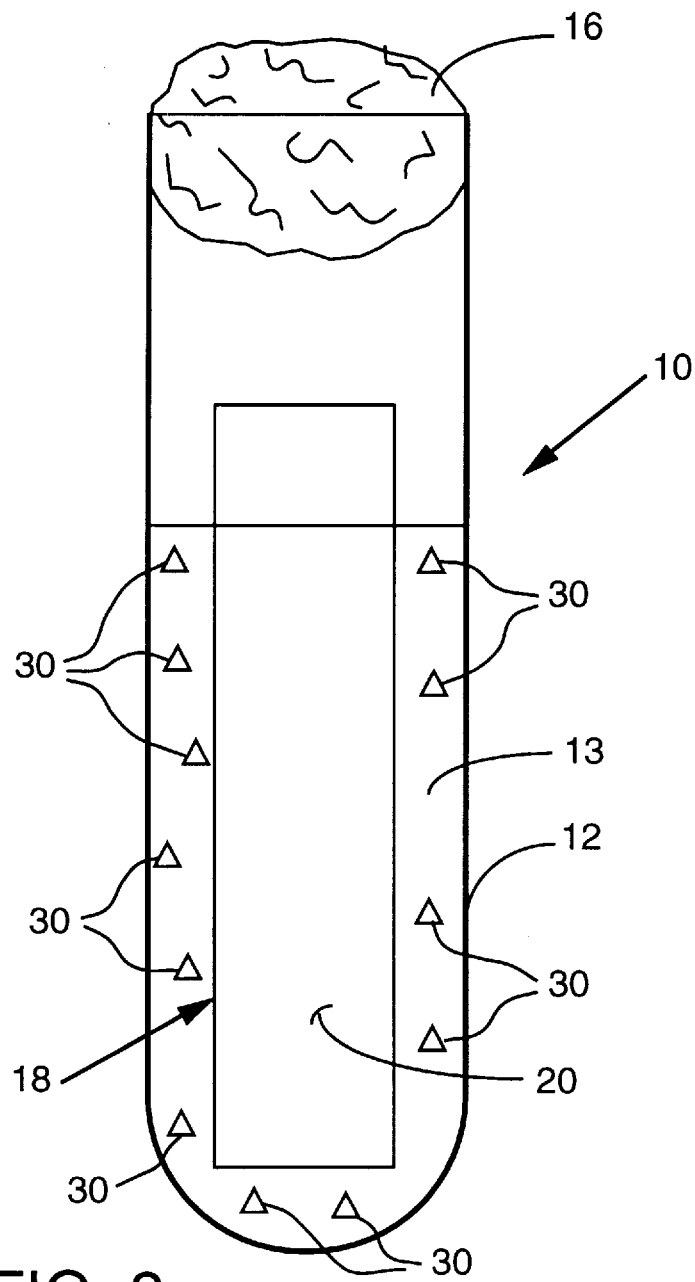
FIG. 2 is a view similar to FIG. 1 only showing the chemicals added to the aqueous solution for adjusting the pH thereof.
Figure 3:
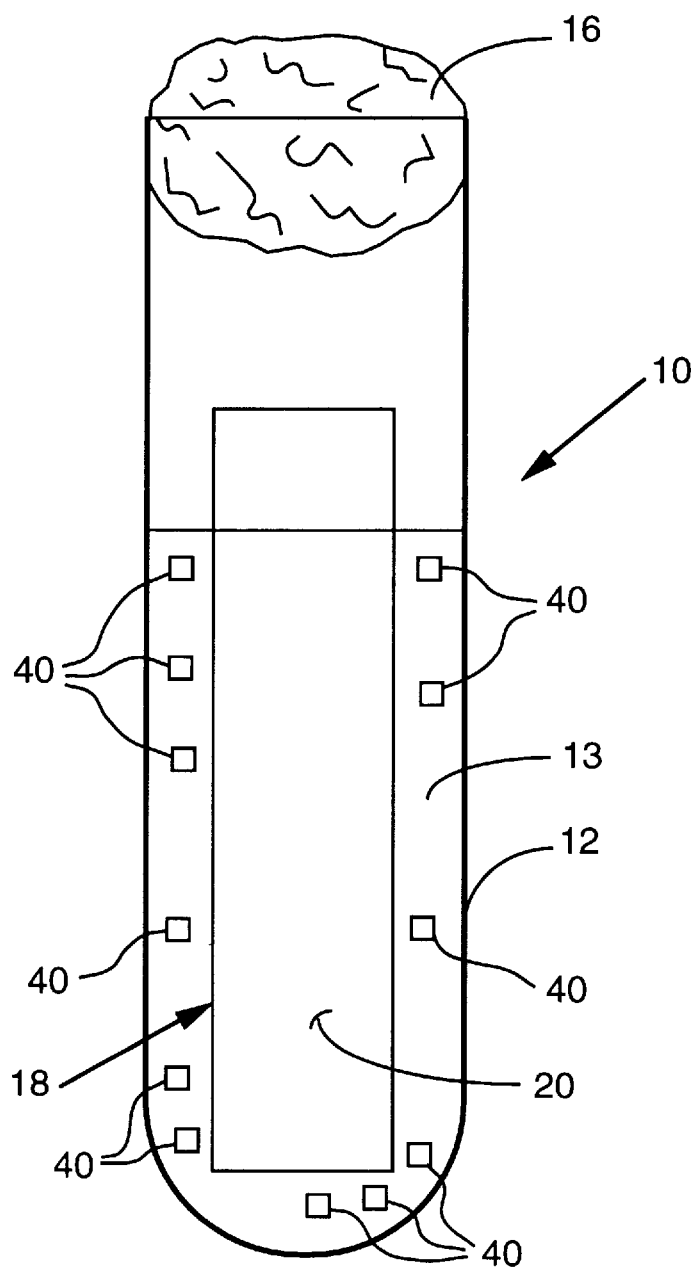
FIG. 3 is a view similar to FIG. 1 only showing the chemicals added to the aqueous solution for mimicking the electrolyte level of the aqueous solution.

In accordance with the invention, the aqueous solution 13 can be adjusted to mimic the in vivo "clinical conditions" of the patient. By "clinical conditions" it is meant at least one of the following: (i) the pH of the in vivo milieu of the patient where the paraffinophilic microorganism can be found and (ii) the electrolyte levels of a patient's blood where paraffinophilic microorganisms can be found. Adjusting the aqueous solution can be effected by numerous different methods. Adjusting the pH of the aqueous solution can be accomplished by adding hydrochloric acid (HCl) to obtain a more acidic solution or by adding sodium hydroxide (NaOH) or potassium hydroxide (KOH) in order to obtain a more basic solution. The chemicals for adjusting the pH of the aqueous solution are represented as reference character number 30 in FIG. 2. Electrolytes such as one or more selected from the group consisting of sodium, potassium, chloride, magnesium, phosphate and calcium, can be added to the solution in desired quantities in order to mimic the electrolytes in the blood of a patient from which a blood sample which may contain the microorganism is obtained. The chemicals for mimicking the electrolyte level of the aqueous solution are represented as reference character number 40 in FIG. 3.

Paraffinophilic microorganisms that can be identified using the method of the invention include at least one of the paraffinophilic microorganisms selected from the group consisting of Micrococcus Paraffinae; Corynebacterium Simplex; Ahnl; Mycococcus (Rhodococcus) Cinnabareus; Ahnl. Mycococcus (Rhodoc) Rhodochrous; Mycobact. Perrugosum Var. Athanicum; Mycobact. Rubrum Var. Propanicum; Mycobacterium Hyalinum; Mycobacterium Lacticola; Mycobacterium Album, M. Luteum; Mycobacterium Microti; Mycobacterium Rubrum, Mycobacterium Phlei.; Mycobacterium Phlei, M. Smegmatis; Mycobacterium Testudo; Mycobacterium-Avium-Intracellulare; Nocardia Spp.; Actinomyces; Candida Lipolytica; Candida Tropicalis, Torulopsis Colliculosa; Monila Sp., Hansenula Sp., Torula rossa; Penicillium Sp.; IHNL. Aspergillus Flavus; Aspergillus sp., Penicillium Sp.; Citromyces Sp., Scopulariopsis Sp.; Pseudomonas Fluorescens Liquefaciens; Ahnl, Pem. Fluorescens Denitrificans; Pseudomonas Aeruginosa.

EXAMPLE 1

An AIDS patient comes to an emergency room at a, hospital complaining of severe abdominal pain. A, gastroenterologist uses a gastrointestinal scope to obtain a, specimen of the patient's stomach fluid. The scope indicates that the pH in the patient's stomach is 1.5. In the meantime, a lab technician using the apparatus of the Figure adjusts the pH of the aqueous solution 13 by adding HCl thereto so that the aqueous solution 13 has a pH of 1.5. Thus, the pH in the patient's stomach is mimicked by the pH of the aqueous solution in the apparatus shown in the Figure. After this, the specimen of stomach fluid taken by the gastroenterologist: from the patient is inoculated into the receptacle 12 holding a paraffin coated slide 18. After about eight days a growth appears on the paraffin coated slide 18. The growth is then analyzed by the method and apparatus disclosed in U.S. Pat. No. 5,153,119 to determine whether MAI is present.

EXAMPLE 2

An AIDS patient comes to an emergency room complaining of high fever and apparently has pneumonia. The physician suspects that there is an infection caused by *Nocardia bactereremia*. As is standard in almost every emergency room, a chemical screen ("CSS") is performed on a blood specimen obtained from the patient. The CSS lists the electrolyte content of the patient's blood. The electrolyte content is communicated to a lab technician who in turn adjusts the aqueous solution 13 in the receptacle 12 holding the paraffin coated slide 18. For example, the CSS reveals that the patient has a sodium level of 120. The lab technician adjusts the sodium level of the aqueous solution (for example, distilled water) by adding sodium thereto in order to mimic the 120 level of sodium found in the patient's blood. The blood specimen is then inoculated into the adjusted aqueous solution. After about two days a growth appears. The growth is analyzed and is found to be, indeed, *Nocardia bactereremia*.

It will be appreciated that a method for identifying a paraffinophilic microorganism has been disclosed in which the aqueous solution in which the paraffin coated slide and the microorganism are placed is adjusted to mimic the in viva clinical conditions of a patient from whom the specimen containing the paraffinophilic microorganism to be identified is obtained. The method is effective and efficient and does not involve the use of expensive and complicated equipment. An associated apparatus is also disclosed.

While specific embodiments of the invention have been disclosed, it will be appreciated by those skilled in the art that various modifications and alterations to those details could be developed in light of the overall teachings of the disclosure. Accordingly, the particular arrangements disclosed are meant to be illustrative only and not limiting as to the scope of the invention which is to be given the full breadth of the appended claims and any and all equivalents thereof.

What is claimed is:

1. An apparatus to facilitate determination of the presence or absence of a paraffinophilic microorganism in a specimen taken from a patient having in vivo clinical conditions, said apparatus comprising:

a receptacle for holding an aqueous solution;

a paraffin coated slide for placement into said receptacle; and chemicals to adjust said aqueous solution so that a pH of said aqueous solution is generally equal to a pH of said specimen.

2. The apparatus of claim 1, wherein said chemicals are selected from the group consisting of HCl, KOH and NaOH.

3. An apparatus to facilitate determination of the presence or absence of a paraffinophilic microorganism in a blood specimen taken from a patient having in vivo clinical conditions, said apparatus comprising:

a receptacle for holding an aqueous solution;

a paraffin coated slide for placement into said receptacle; and chemicals to adjust said aqueous solution so that an electrolyte level of said aqueous solution is generally equal to an electrolyte level in said blood specimen.

4. The apparatus of claim 3, wherein said chemicals include at least one of the group consisting of sodium, potassium, chloride, magnesium, phosphate and calcium.

* * * * *

UNITED STATES PATENT AND TRADEMARK OFFICE
CERTIFICATE OF CORRECTION

PATENT NO. : 5,882,920

DATED : March 16, 1999

INVENTOR(S) : Mitchell S. Felder et al.

It is certified that error appears in the above-identified patent and that said Letters Patent is hereby corrected as shown below:

Column 2, line 40, delete the "." after the word "not".

Column 4, line 18, "viva", should read --vivo--, as originally submitted.

Signed and Sealed this

Twenty-eighth Day of March, 2000

Attest:

Q. TODD DICKINSON

*Attesting Officer*  *Commissioner of Patents and Trademarks*